United States Patent [19]

Yamafuji et al.

[11] Patent Number: 5,302,262
[45] Date of Patent: Apr. 12, 1994

[54] TASTE SENSING METHOD FOR DISCRIMINATING IN DETAIL TASTE OF SUBSTANCES WITH HIGH REPRODUCIBILITY BY USING ARTIFICIAL LIPID MEMBRANES

[75] Inventors: Kaoru Yamafuji, 1-6-21, Kusagae, Chuo-ku, Fukuoka-shi, Fukuoka-ken; Kiyoshi Toko, 2-8-32-2, Miwadai, Higashi-ku, Fukuoka-shi, Fukuoka-ken; Kenshi Hayashi, 2-14-18-407, Takatori, Sawara-ku, Fukuoka-shi, Fukuoka-ken; Hidekazu Ikezaki, Isehara; Rieko Toukubo, Hadano, all of Japan

[73] Assignees: Anritsu Corporation, Tokyo; Kaoru Yamafuji, Fukuoka; Kiyoshi Toko, Fukuoka; Kenshi Hayashi, Fukuoka, all of Japan

[21] Appl. No.: 64,342

[22] Filed: May 19, 1993

Related U.S. Application Data

[63] Continuation of Ser. No. 725,655, Jul. 3, 1991, abandoned.

[30] Foreign Application Priority Data

Jul. 4, 1990 [JP] Japan .................................. 2-176584

[51] Int. Cl.$^5$ ........................................... G01N 27/26
[52] U.S. Cl. ........................... 204/153.12; 204/153.1; 204/403; 204/418; 435/291; 435/817
[58] Field of Search ............... 204/400, 403, 416, 418, 204/153.1, 153.12, 412, 434; 435/291, 817

[56] References Cited

U.S. PATENT DOCUMENTS

| H201 | 1/1987 | Yager ................... 436/151 |
| 3,556,950 | 1/1971 | Dahms ................. 204/153.1 |
| 3,925,168 | 12/1975 | Costas ................. 204/434 |
| 4,119,406 | 10/1978 | Clemens ............... 422/81 |
| 4,146,437 | 3/1979 | O'Keefe ............... 204/412 |
| 4,251,290 | 2/1981 | Gomez ................. 136/206 |
| 4,490,216 | 12/1984 | McConnell ............ 204/153.1 |
| 4,637,861 | 1/1987 | Krull .................. 204/418 |
| 4,661,235 | 4/1987 | Krull et al. .......... 204/153.1 |
| 4,801,540 | 1/1989 | Hiatt et al. .......... 435/172.3 |
| 4,849,343 | 7/1989 | Krull .................. 204/153.12 |
| 4,925,969 | 5/1990 | Takahashi et al. ..... 560/41 |

FOREIGN PATENT DOCUMENTS 0158834 10/1985 European Pat. Off.
158834 3/1985 Fed. Rep. of Germany.
63241354 10/1977 Japan.

OTHER PUBLICATIONS

McBurney, D. H.: 1974, "Are There Primary Tastes For Man?", Chemical Senses and Flavor 1, pp. 17–29.
O'Mahoney, M. and Ishii, R.: 1987, "Umami: A Basic Taste, The Umami Taste Concept: Implications for the Dogma of Four Basic Tastes", pp. 75–93.
Chemical Formulas of "Umami".
Kurihara, K.: "Receptor mechanisms of taste and olfaction", Faculty of Pharmaceutical Sciences, Hokkaido University. 60 (7) 1991, pp. 682–689.

(List continued on next page.)

*Primary Examiner*—John Niebling
*Assistant Examiner*—Bruce F. Bell
*Attorney, Agent, or Firm*—Frishauf, Holtz, Goodman & Woodward

[57] ABSTRACT

A method for separately detecting tastes of a plurality of similar samples by using a taste sensor employing a lipid membrane includes first, second, third, and fourth steps. In the first step, a reference solution having a taste identical or similar to one of the plurality of samples is prepared. In the second step, the reference solution is measured by using the taste sensor. In the third step, one of the plurality of samples is measured by using the taste sensor. In the fourth step, a relative value $Vi - V0$ of the sample is calculated from the measured value $V0$ of the reference solution and the measured value $Vi$ of the sample. The second to fourth steps are repeatedly performed for each of the plurality of samples.

13 Claims, 15 Drawing Sheets

OTHER PUBLICATIONS

Biophys. J., vol. 59, Jun. 1991, pp. 1218–1234.
Biochemistry 1987, 26, pp. 6141–6145.
"Effects (Permeability, Surface Potential) of Primary Tastes on Lipid Membrane . . . " (employed in present invention).
"Membrane", 12 (4), 231–237 (1987).
Documents describing interaction between the taste substances and lipid membrane in light of the present invention.
FIG. 8 - "Response patterns to substances which taste similar to humans", etc.
Sensors and Actuators, B, 2 (1990) 205–213.
Transducers '87, pp. 793–796, K. Toko, et al.
C-II, vol. J74–C-II, No. 5, pp. 434–442 (1991): "Multi--Channel Taste Sensor with Artificial Lipid Membranes" & Partial Translation of p. 439.
Technical Digest of 10th Sensor Symposium, 1991, pp. 173–176.
United States Statutory Invention H201, Published Jan. 6, 1987–Inventor Paul Yager.
C. Pfaffman, Handbook of Physiology, Section 1, Neurophysiology vol. 1, ed. by J. Field, American Physiological Society, Washington, D.C., 1959, p. 507.
Proceedings of the 5th Sensor Symposium, 1985, pp. 231–236 Kiyoshi Toko et al.
Agri. Biol. Chem., 50(11), pp. 2709–2714, 1986 Satoru Iiyama et al.
Membrane, 12(4), pp. 231–237, 1987, Satoru Iiyama et al.
Proc. of the 22nd Jap. Symp. on Taste and Smell (1988) pp. 213–216; Kiyoshi Toko et al.
Technical Digest of the 7th Sensor Symposium, 1988; pp. 127–130; Kiyoshi Toko et al.
Agric. Biol. Chem., 53(3), pp. 675–681, 1989; Satoru Iiyama et al.
Sensors and Actuators, 16(1989) pp. 25–42; K. Hayashi et al.
Sensors and Materials, 1–6(1989), pp. 321–334 K. Hayashi et al.
Japanese Journal of Applied Physics vol. 28, No. 8, Aug., 1989, pp. 1507–1512; Kenshi Hayashi et al.
MBE 89-109 pp. 87–94 Masami Yamanaka et al.
Technical Digest of the 9th Sensor Symposium, 1990, pp. 193–196; Kiyoshi Toko et al.

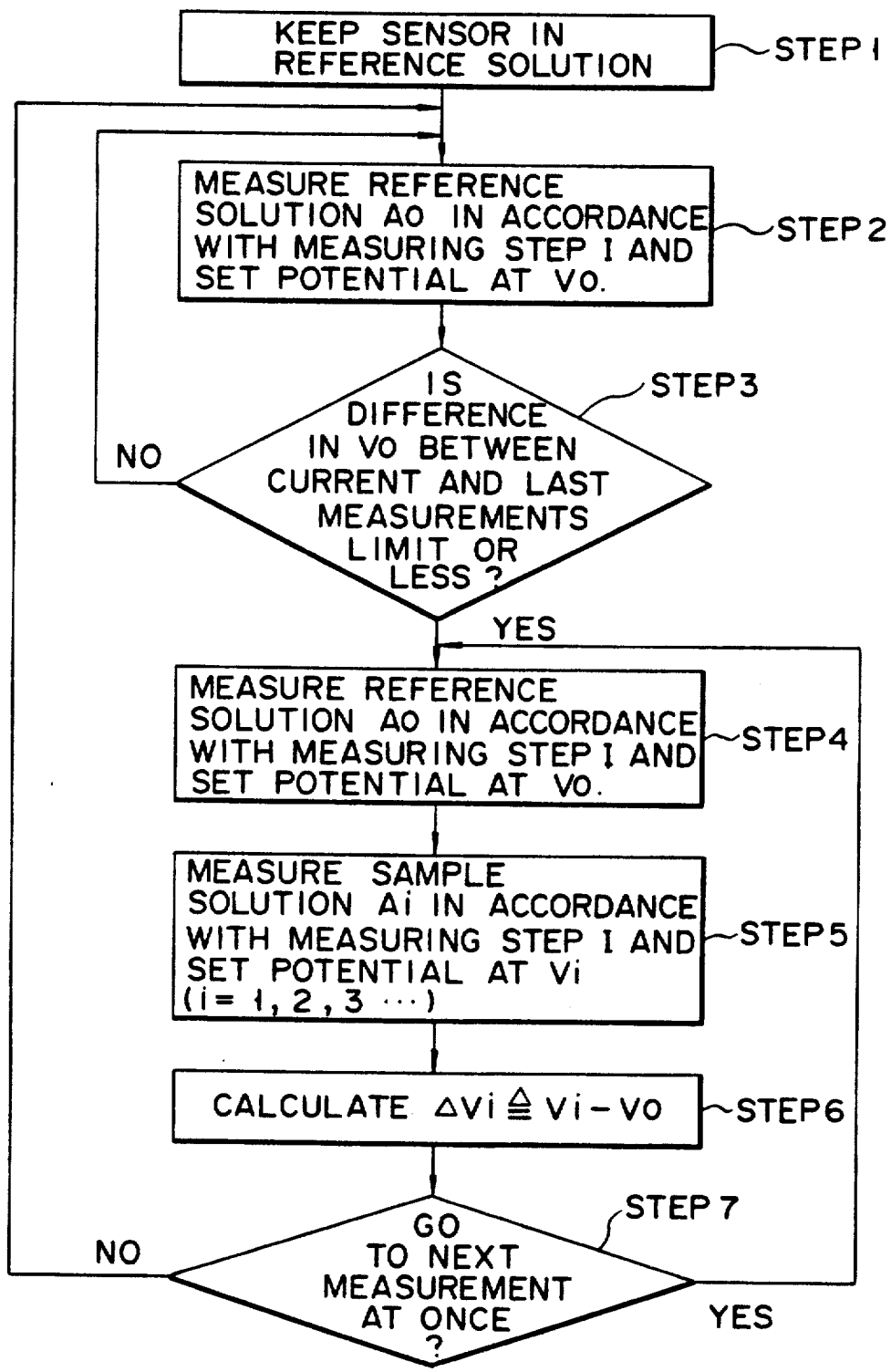
F I G. 1A

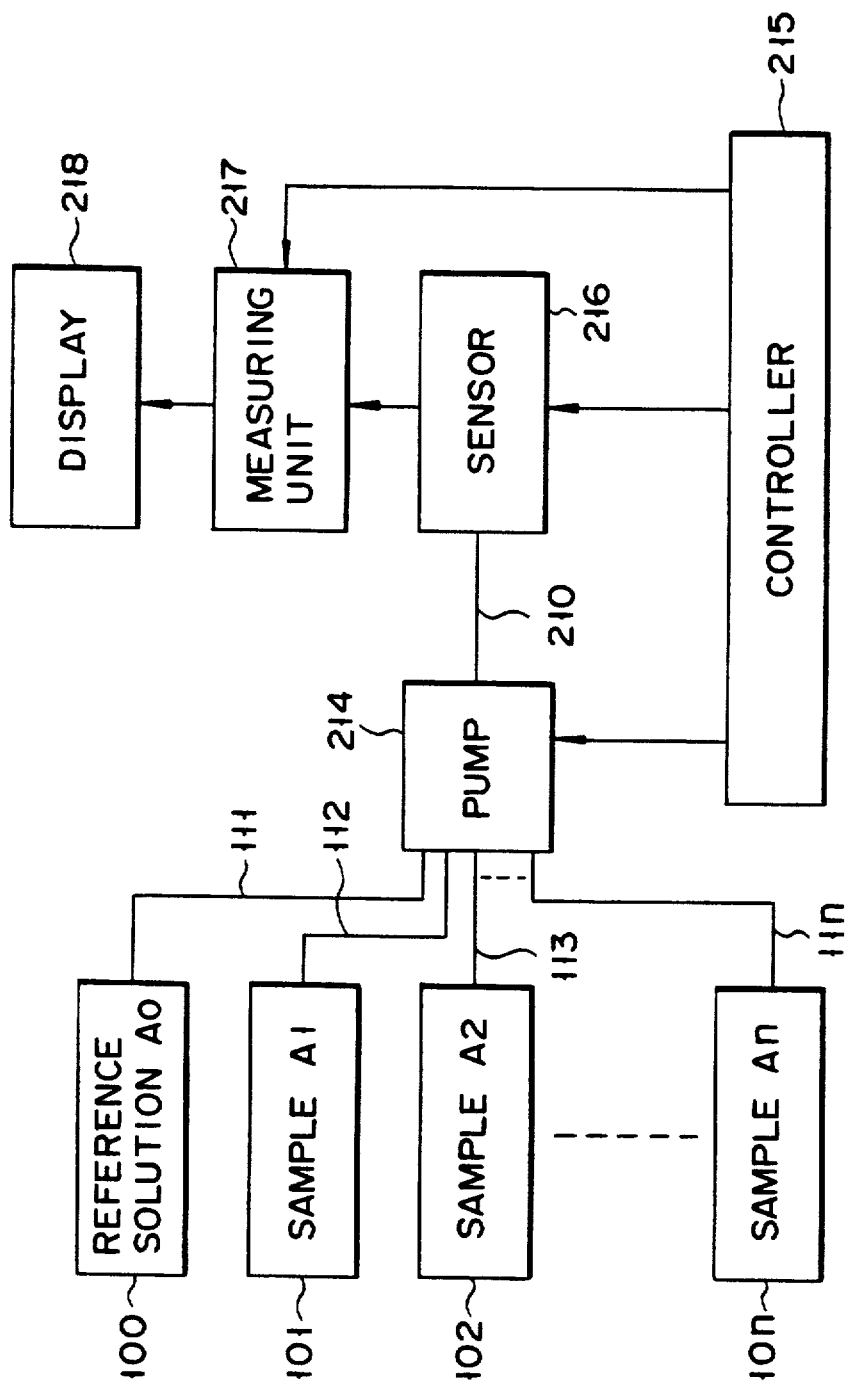
F I G. 1D

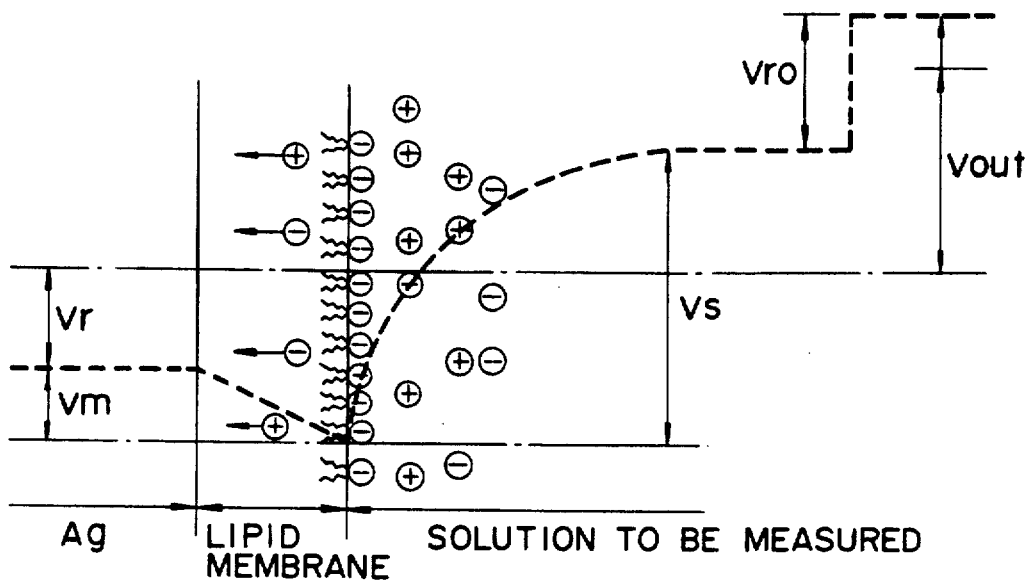

FIG. 2B

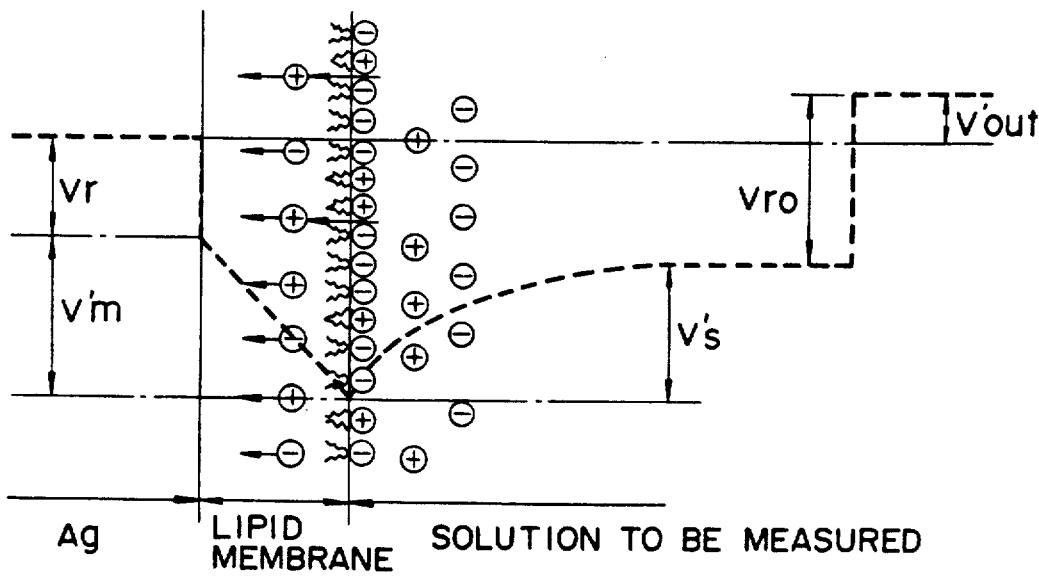

| | |
|---|---|
| Vro | : Ag\|AgCl OXIDATION-REDUCTION POTENTIAL (REFERENCE ELECTRODE) |
| Vr, Vr' | : OXIDATION-REDUCTION POTENTIAL (Vr ≒ Vr') |
| Vs, Vs' | : SURFACE POTENTIAL |
| Vm, V'm | : INTRAMEMBRANE POTENTIAL |
| Vout, V'out | : SENSOR OUTPUT POTENTIAL (Vout = Vro + Vs + Vm + Vr) |

⇝⊖ : LIPID MOLECULE

⊕ / ⊖ : TASTE SUBSTANCE MOLECULE ADSORBED TO LIPID MOLECULE COMPARATIVELY WEAKLY (EX. SALT)

⇝⊕ : TASTE SUBSTANCE MOLECULE STRONGLY ADSORBED TO LIPID MOLECULE (EX. BITTERNESS)

FIG. 2C

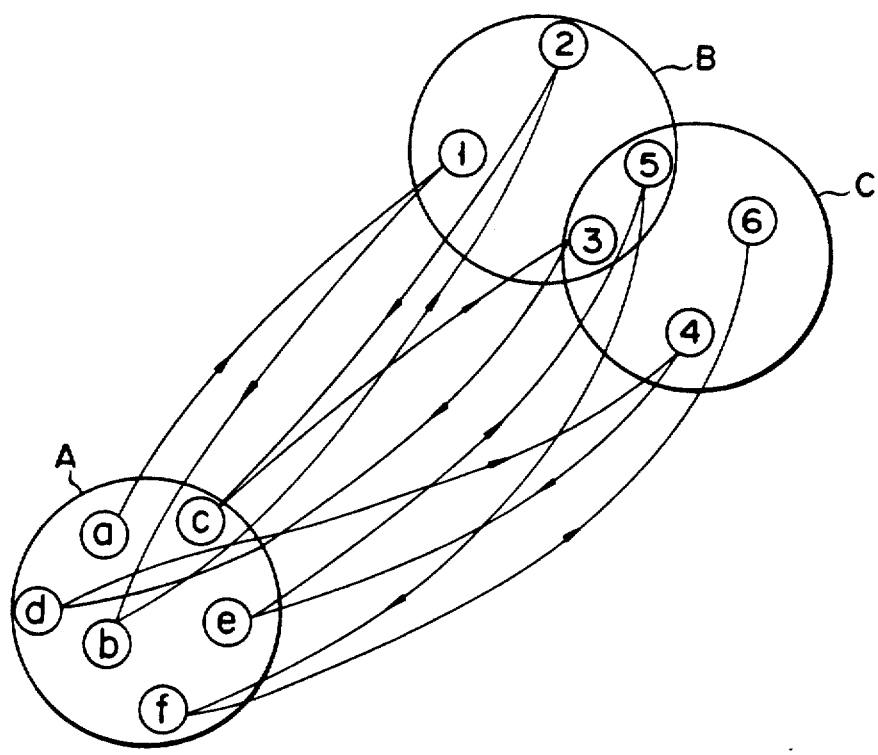
F I G. 3A
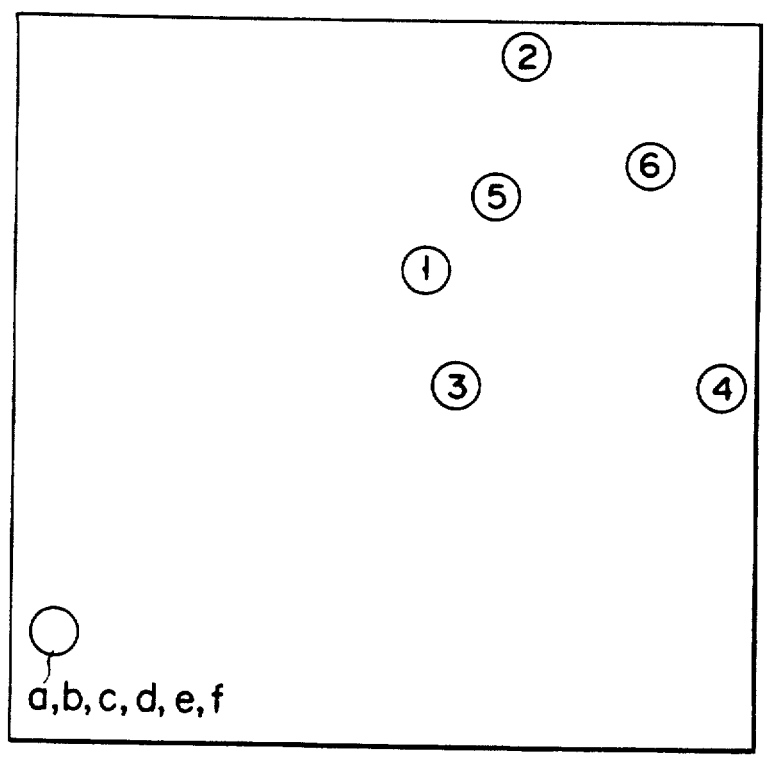
F I G. 3B

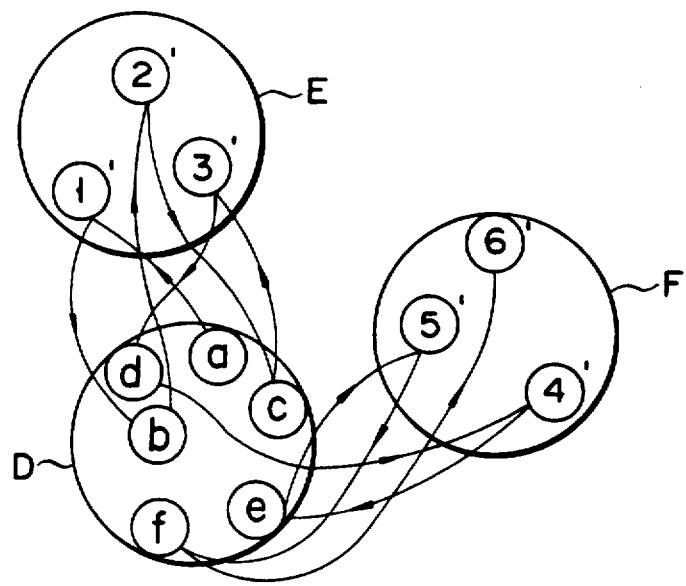
F I G. 4A
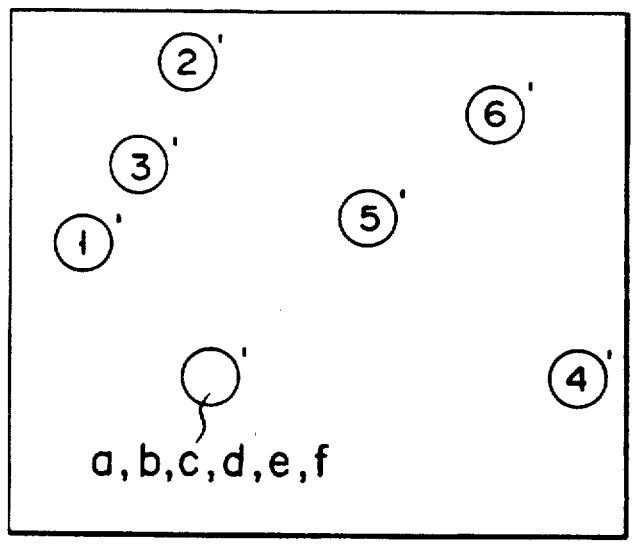
F I G. 4B

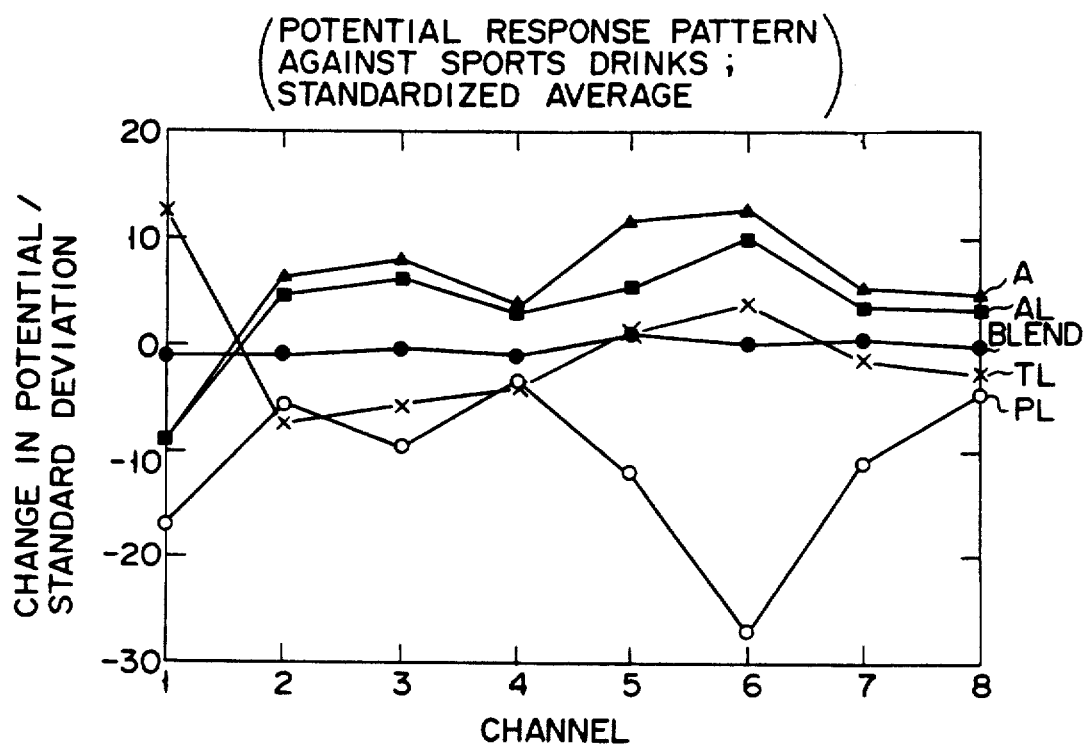
F I G. 7A
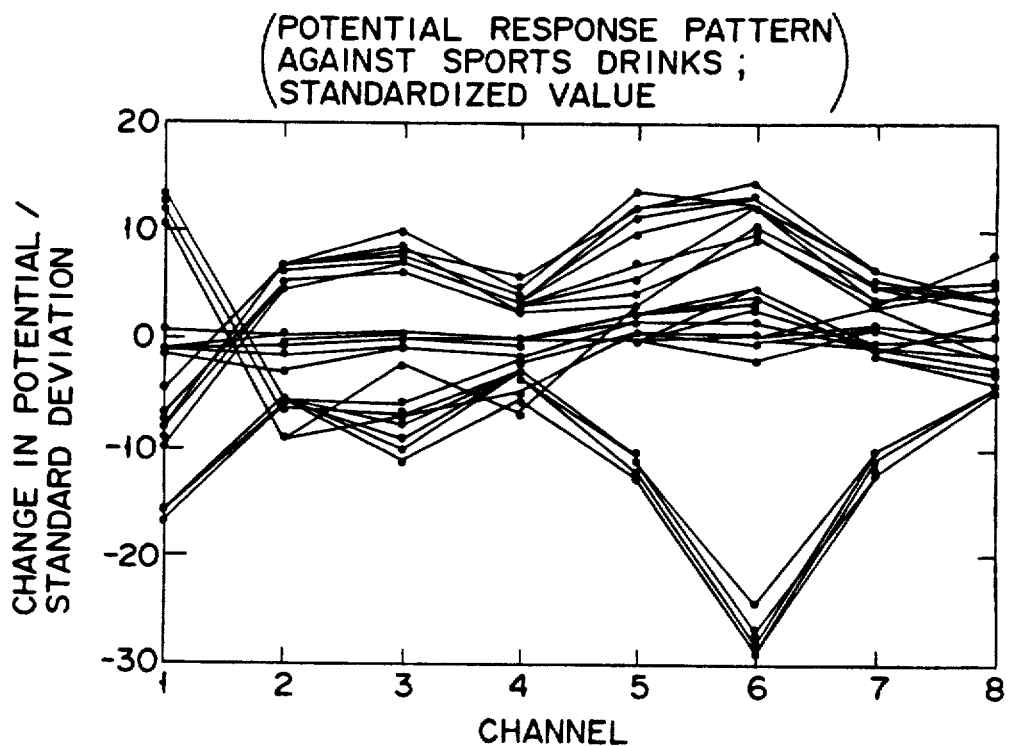
F I G. 7B

TASTE SENSING METHOD FOR DISCRIMINATING IN DETAIL TASTE OF SUBSTANCES WITH HIGH REPRODUCIBILITY BY USING ARTIFICIAL LIPID MEMBRANES

This application is a continuation of application Ser. No. 07/725,655, filed Jul. 3, 1991 (abandoned).

BACKGROUND OF THE INVENTION

1. Field of the Invention

The present invention generally relates to a taste sensing method using artificial lipid membranes.

The present invention also relates to a technique for detecting and measuring a difference in taste of beverages and comestibles, which is formerly difficult to measure by an artificial sensor, by utilizing a sensor that can replace the sense of taste as one of the five senses of human.

Furthermore, the present invention relates to a technique for detecting a difference in taste of food, e.g., beverage and alcohol goods to drink. Hence, the present invention relates to a technique which enables quality control of beverages and alcohols at the factories by an automated machine system without using a human labor.

2. Description of the Related Art

Basic taste elements are said to consist of saltiness, sweetness, bitterness, sourness, and "Umami". These elements are exibited in different degrees, respectively. Let us suppose that a difference between these tastes that can be evaluated by human senses or a difference between different degrees of the same taste, e.g., saltiness that can be evaluated by human senses, can be grasped as a physically measurable amount, and that a measurable taste or a measurable difference in taste (comparative or relative taste) is referred to as taste in this specification.

The present applicants have previously filed a patent application of an invention entitled "Taste Sensing System Using Artificial Lipid Membranes" (U.S. patent application Ser. No. 07/555,163). The specification and its accompanying drawings show that a lipid molecular membrane, having a matrix structure in which a lipid material comprising hydrophobic molecules and hydrophilic molecules is fixed in a polymer matrix and the hydrophilic molecules of the lipid are arranged in the matrix surface, can serve as a taste sensor that can replace the human sense of taste.

The outline of such a taste sensor will be briefly described. Namely, assume that a partial description of the above application is incorporated hereinafter.

FIG. 9 shows a schematic view of formation of such a lipid molecular membrane by an expression method used in a designing method of a chemical substance. Each lipid molecule shown in FIG. 9 includes a hydrophilic group a, i.e., a hydrophilic portion a represented by a spherical portion which is indicated by a circle, and a chain structure b (e.g., an alkyl group) of a hydrocarbon in which an atomic array extends. In FIG. 9, two chains extend to represent one molecule, thereby constituting molecule group as a whole. This chainportion of the hydrocarbon is a hydrophobic portion b. These lipid molecules 31 are received in a surface structure of a matrix 33 of a membrane material 32, i.e., in the surface of a planar wide micro structure and inside the matrix 33 so that they are dissolved therein (e.g., 31' in FIG. 9).

The molecules 31 are accommodated such that the hydrophilic portions are arranged on the surface.

FIGS. 10A and 10B show a multi-channel taste sensor using such a lipid molecular membrane. FIGS. 10A and 10B show three sensing parts of multi-channel electrodes.

In FIGS. 10A and 10B, holes having a diameter of 1.5 mm are formed in a base material, and silver rods are inserted in the holes to provide electrodes. The lipid molecular membrane is applied on the base member to contact the electrodes through a buffer layer.

FIG. 11 shows a taste measuring system using the multi-channel taste sensor described above.

An aqueous solution of taste substances was prepared and put as a solution 11 to be measured in a vessel 12 such as a beaker. A taste sensor array 13 manufactured by arranging lipid membranes and electrodes on an acrylic plate (base member) as described above was put in each solution 11 to be measured. Before the sensor array 13 was used, an electrode potential was stabilized by soaking in an aqueous solution of potassium chloride having a concentration of 1 m mol/l. In FIG. 11, black dots 14-1, ..., 14-8 represent the lipid membranes.

A reference electrode 15 was prepared as an electrode for generating a reference potential of measurement and put in the solution to be measured. The taste sensor array 13 and the reference electrode 15 were separated from each other by a predetermined distance. The surface of the electrode 15 was covered with a material prepared by fixing potassium chloride having a concentration of 100 m mol/l in agar-agar as a buffer layer 16. Therefore, the electrode system is constituted by silver 2 | silver chloride 4 | lipid membrane 3 (14) | solution to be measured 11 | buffer layer (potassium chloride 100 m mol/l) 16 | silver chloride 4 | silver 2.

Electrical signals from the lipid membranes are supplied as 8-channel signals to buffer amplifiers 19-1, ..., 19-8 via lead wires 17-1, ..., 17-8, respectively. Outputs from the buffer amplifiers 19 are selected by an analog switch (8 channel) 20 and loaded to an A/D converter 21. An electrical signal from the reference electrode 15 is also supplied as a reference potential to the A/D converter 21 via a lead wire 18. A difference between the reference potential and a potential from the membrane is converted into a digital signal so as to process in a micro computer 22 and display on an X-Y recorder 23.

In this example, an 8-channel taste sensor is used. The channels comprise a lipid molecular membrane shown in Table 1 which have different response characteristics with respect to a taste in order to obtain large number of taste information, thus reproducing the human sense of taste.

TABLE 1

| No. | Name (Abbreviation) |
| --- | --- |
| 1. | dioctylphosphate ($2C_8POOH$) |
| 2. | cholesterol |
| 3. | trioctylmethyl ammonium chloride (TOMA) |
| 4. | oleic acid |
| 5. | n-octadecylchloride |
| 6. | diphenyl phosphate |
| 7. | decylalcohol |
| 8. | dioctadecyldimethylammonium bromide (DOAB) |
| 9. | lecithin |
| 10. | trimethyl stearyl ammoniumchloride (TMSA) |
| 11. | oleylamine |

It is assumed that an electrode of the taste sensor has a potential profile as shown in FIG. 12. In FIG. 12, an intramembrane potential gradient is expressed as 0 (positive and negative charges are uniformly distributed in the membrane).

When a taste is to be detected and measured by using the lipid molecular membrane (also called simply as a lipid membrane) described above, several new countermeasures are demanded.

For example, when taste quality control is to be performed for discriminating foods having only slightly different tastes or manufacturing foods whose only slightly different tastes must be discriminated, a difference in taste sensor outputs becomes small accordingly. For this reason, a measured value obtained by the sensor must have good reproducibility, and a measured value must not vary.

However, with the conventional taste measurement using the lipid membrane described above, such new demands cannot be satisfied.

SUMMARY OF THE INVENTION

It is, therefore, an object of the present invention to provide a new and improved taste sensing method using artificial lipid membranes which can discriminate in detail taste of substances with high reproducibility.

According to the one aspect of the present invention, there is provided a method for separately detecting tastes of a plurality of similar samples by using a taste sensor employing a lipid membrane, comprising the steps of:

(a) preparing a reference solution having a taste identical or similar to one of the plurality of samples;

(b) measuring the reference solution by using the taste sensor to obtain a measured value V0;

(c) measuring one of the plurality of samples by using the taste sensor to obtain a measured value Vi; and (d) calculating a relative value Vi−V0 of a reference value of the sample from the measured value V0 of the reference solution and the measured value Vi of the sample, wherein the steps (b) to (d) are repeatedly executed for each of the plurality of samples.

According to another aspect of the present invention, there is provided a method for individually detecting tastes of a plurality of similar samples by using a taste sensor employing a lipid membrane, comprising the steps of:

(a) preparing a reference solution having a taste identical or similar to one of the plurality of samples;

(b) measuring one of the plurality of samples by using the taste sensor to obtain a measured value Vi;

(c) measuring the reference solution by using the taste sensor to obtain a measured value Vo; and (d) calculating a relative value Vi−V0 of a reference value of the sample from the measured value V0 of the reference solution and the measured value Vi of the sample, wherein the steps (b) to (d) are repeatedly executed for each of the plurality of samples.

According to still another aspect of the present invention, there is provided a method for detecting taste of a sample, the method comprising the steps of:

biasing a taste sensor comprising a lipid membrane representing a potential response in response to the taste of the sample, by dipping the taste sensor in a reference solution having a taste similar to the taste of the sample;

periodically stimulating the taste sensor by intermittently dipping and removing the taste sensor in and from the reference solution or the sample a predetermined number of times;

synchronously measuring the potential response of the taste sensor with respect to the reference solution and the sample at substantially the same timing as that at which a membrane potential of the taste sensor shows a stabilizing tendency during the stimulating step; and evaluating the taste of the sample, after the measuring step, in accordance with a relative value between a potential response of the taste sensor with respect to the reference solution and a potential response of the taste sensor with respect to the sample.

Additional objects and advantages of the invention will be set forth in the description which follows, and in part will be obvious from the description, or may be learned practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principle of the invention, in which:

FIGS. 1A, 1B, and 1C are flow charts of measuring steps, in which FIG. 1A is a flow chart of the measuring steps of the present invention, FIG. 1B is a flow chart of an example of the measuring steps commonly employed in steps 2, 4, and 5 of the measuring steps of the present invention, and FIG. 1C is a flow chart of the conventional measuring steps;

FIG. 1D is a block diagram of a taste sensing system applied to the preferred embodiments of the present invention;

FIGS. 2A, 2B, and 2C show potential profiles of taste sensor electrodes;

FIGS. 3A and 3B schematically show the measurement result obtained by the conventional measuring method, in which FIG. 3A schematically shows the measurement result by way of measured potentials, and FIG. 3B schematically shows the measurement result by way of potential differences between potentials of sample solutions and a potential of the reference solution in each measurement;

FIGS. 4A and 4B schematically show the measurement result obtained by the measuring method of the present invention, in which FIG. 4A shows the measurement result by way of the measured potentials, and FIG. 4B schematically shows the measurement result by way of potential difference between potentials of sample solutions and a potential of the reference solution in each measurement;

FIGS. 7A and 7B show intramembrane potential response patterns with respect to sports drinks, in which FIG. 7A shows the pattern obtained by using only the averages of the respective samples in the respective channels, and FIG. 7B shows the pattern obtained by using all the measured values of the respective samples of the respective channels;

FIGS. 8A and 8B show intramembrane potential response patterns with respect to beer, in which FIG. 8A shows the pattern obtained by using only the averages of the respective samples of the respective channels, and FIG. 8B shows the pattern obtained by using all the measured values of the respective samples of the respective channels;

FIGS. 10A and 10B are schematic views of a taste sensor, in which FIG. 10A is a front view of the same, and FIG. 10B is a sectional view of the same;

DETAILED DESCRIPTION OF THE PREFERRED EMBODIMENTS

Figure 1B:
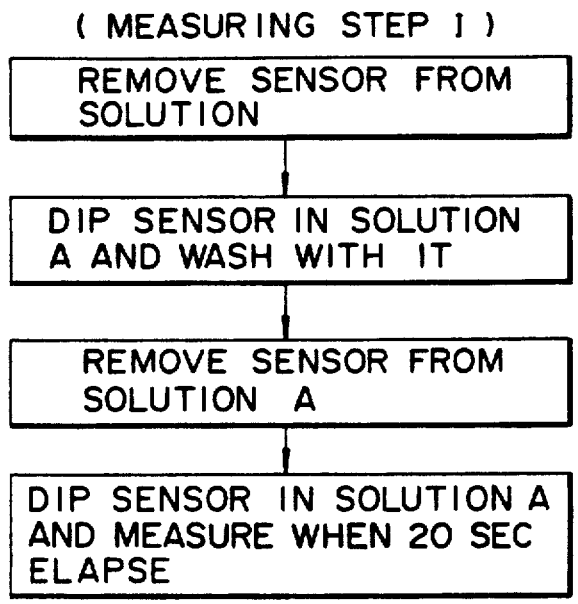

Reference will now be made in detail to the presently preferred embodiments of the invention as illustrated in the accompanying drawings, in which like reference characters designate like or corresponding parts throughout the several drawings.

The outline of the present invention will be described first.

More specifically, in taste measurement using a lipid membrane, the sensor itself and the way to use it must be improved to meet a new demand of discriminating a taste of a substance in detail and with good reproducibility. A consideration will be made on the reproducibility of the measured value of the sensor. The following two factors are considered to be the major factors that degrade the reproducibility (refer to FIG. 2A).

(1) Instability of Intramembrane Potential

When a beverage (sample solution) as a measurement target permeates into a lipid membrane, an intramembrane potential Vm occurs inside the lipid membrane and on the lipid membrane surface. The intramembrane potential seems to fluctuate depending on the surrounding environment. According to numerous measurement examples, the intramembrane potential is influenced by, e.g., adding a mechanical vibration to the sample solution to be measured, repeating extraction and dipping of the lipid membrane from and into the sample solution, a remaining sample solution of a preceding measurement on the lipid membrane, and the like. Therefore, the intramembrane potential does not become constant.

Figure 2A:
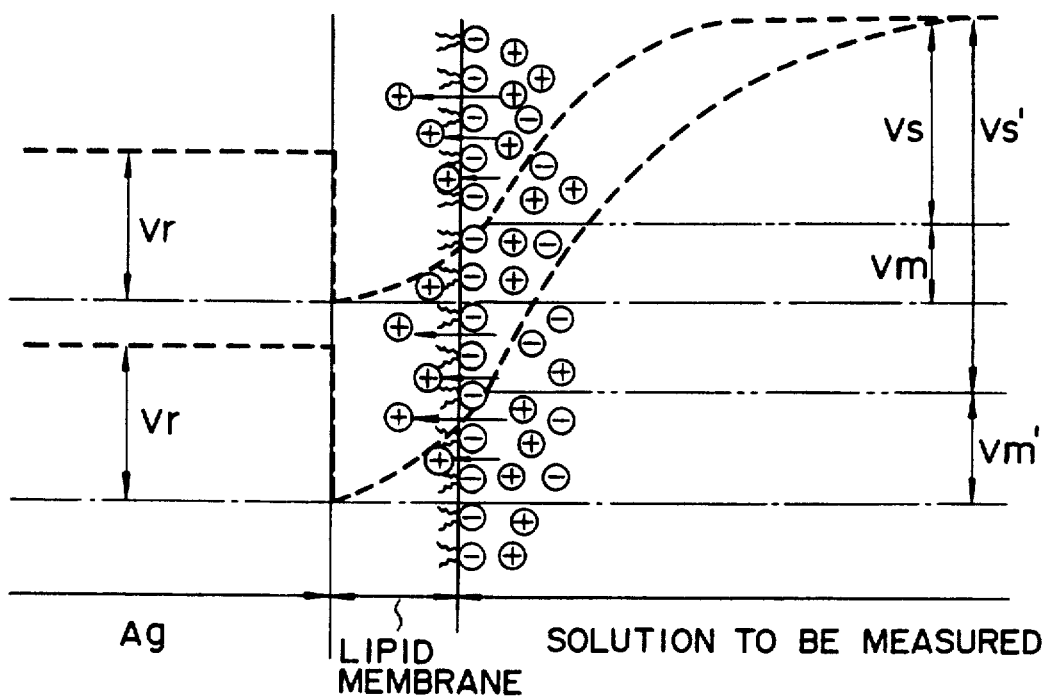

As shown in FIG. 2A, a potential Vm under a certain condition can become Vm' even if the same sample solution to be measured is used, by, e.g., adding a mechanical vibration.

(2) Instability of Surface Potential

Once a sample solution is measured by a certain lipid membrane, the taste molecules permeates into the lipid membrane or (particularly, taste molecules having high adsorptibity such as a bitterness substance) attaches the surface of the lipid membrane. As a result, the charge density on the surface of the lipid membrane changes and the response characteristics change. Then, even if the same sample to be measured is used, the surface potential in the lipid membrane changes, e.g., Vs and Vs' in FIG. 2A. A fluctuation in surface membrane potential due to a variation in charges in the surface of the lipid membrane is observed as a hysteresis.

FIGS. 2B and 2C will be described in detail. FIGS. 2B and 2C show examples of the potential profile of the taste sensor electrodes employing anionic lipid membranes. FIG. 2B shows a state in which the taste sensor is dipped in the solution to be measured. An electrical double layer is formed by the anions fixed on the membrane surface and the cations in the vicinity of the membrane surface. An ion density profile is generated by the Brownian motion in which the farther from the membrane surface, the lower the ion density, thus forming the diffuse electrical double layer.

The potential on the membrane surface obtained by the diffuse electrical double layer is lower than that of the reference electrode by a potential Vs. The potential profile in the solution to be measured exhibits a curve as shown in FIG. 2B because of the ion density profile.

Ions permeate into the membrane from the solution to be measured. A potential profile is generated in the membrane by a difference in permeation rate between the anions and cations.

FIG. 2C shows a state in which taste substances are adsorbed on the membrane surface. The state of the diffuse electrical double layer is changed by the adsorbed taste substances, and the potential difference with respect to the reference electrode is changed from Vs to Vs'. The intramembrane potential fluctuates due to the following reason. Namely, as the taste substance is adsorbed on the membrane surface, the charge density on the membrane surface is changed, and the state of the taste substance preamble into the membrane is thus changed, resulting in the fluctuation in intramembrane potential. At this time, the potential difference between the side of the solution to be measured and the side of the Ag electrodes is changed from Vm to Vm'.

A potential difference (Vout) measured as an output from the taste sensor is expressed as:

$$Vout \simeq Vro + Vs + Vm + Vr$$

where Vro is the oxidation-reduction potential of the reference electrode which is assumed to be constant, Vr is the oxidation-reduction potential of the Ag electrodes, Vs is the surface potential that fluctuates depending on the measurement target and the condition, and Vm is the intramembrane potential, Vm and Vr being negative in this example.

FIG. 2A is the combination of FIGS. 2B and 2C.

The following three points are noted in the present invention in order to cope with the two major factors described above that degrade the reproducibility.

(1) A reference solution which is an aqueous solution of a substance having a basic taste of the same type as that of the sample solution to be measured and which has a taste similar to that of the sample solution to be measured is prepared. Measurement is performed for the reference solution and the sample solution to be measured.

As a result, a hysteresis is prevented, and the taste measurement is performed by measuring a relative value with respect to the reference solution, thereby decreasing fluctuation in measurement result.

The result of this measurement can be schematically illustrated as FIGS. 3A and 3B. FIG. 3A shows three circles A, B, and C. Each measured membrane potential will be written in a corresponding circle. The center of the circle A indicates the membrane potential of the reference solution of the conventional technique. The measured value fluctuates inside this circle A. Assume that the circles B and C indicate the measured value range of the taste of a certain coffee. Measurement starts with a measured value (a) of the reference solution. Then, the taste of the coffee is measured to be a measured value (1) in the circle B. The process returns to the measurement of the reference solution along an arrow and another value (b) in the circle A is set as the measured value. The process then advances to the measurement of the taste of the coffee as a measurement value (2). The same processes are repeated and the taste of the coffee is measured to be a measured value (3). Likewise, the taste of another coffee as another sample solution is measured to be measured values (4), (5), and (6). In this manner, the circle A indicates the hysteresis range, and the measured value of the taste fluctuates within the ranges of the circles B and C. FIG. 3B shows a fluctuation in relative value obtained by calculating differences between the measured values (1) to (6) and the measured values (a) to e,crc/f/ , respectively. Repetition of the circle A≈the circles B and C is the conventional taste measurement using lipid membranes.

According to the measurement method of the present invention, a reference solution having a taste similar to that of the sample solution to be measured is prepared, and the taste is measured as a difference between the reference solution and the sample solution to be measured. Therefore, the membrane potential does not easily fluctuate between the reference solution and the sample solution to be measured. FIG. 4A is a schematic view showing this method as the movement among circles D, E, and F. The circles D, E, and F are smaller than the circles A, B, and C. Hence, the fluctuation is smaller in FIG. 4A. FIG. 4B shows the differences between measured values (1)' to (6)' and values (a)' to (f)', respectively, in the same manner as in FIG. 3B. In FIG. 3B, the fluctuation is large, and the values of the two samples partially overlap, resulting in a difficulty in discriminating the tastes. In contrast to this, in FIG. 4B, the fluctuation is small, and the discrimination of the tastes is easy.

(2) Measurement is done within short period of time. This prevents the sample solution to be measured from permeating in the membrane.

Figure 5A:
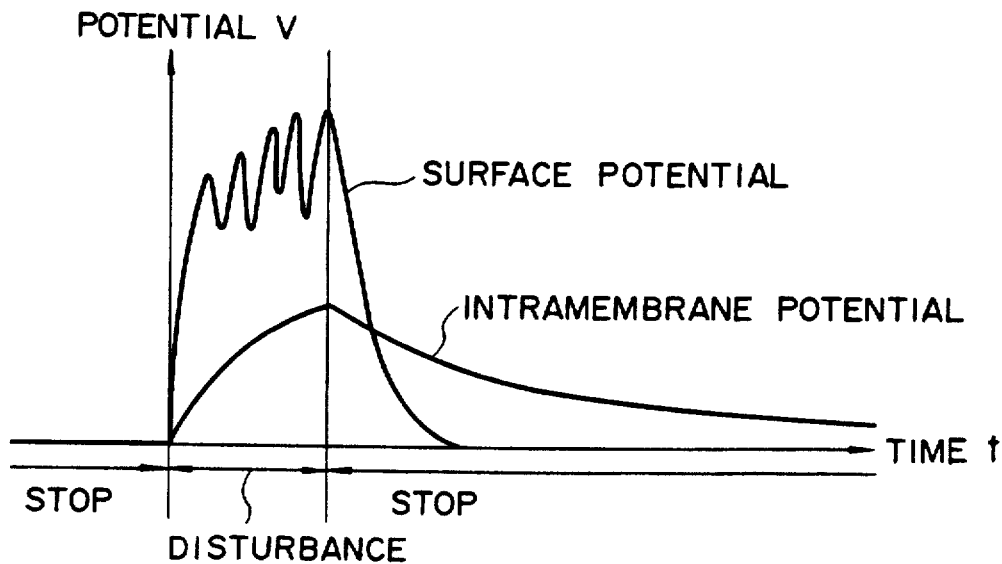
FIGS. 5A and 5B show the changes in surface potential and intramembrane potential over time.

FIG. 5A shows changes in intramembrane potential and surface potential of a lipid membrane potential over time. The axis of abscissa indicates time t and the axis of ordinate indicates a potential V. Assume that a state continuous from the left side of the drawing is disturbed at a time point $t=0$ by externally applying a power. For example, assume that the sensor that has been dipped in the reference solution for a long period of time is abruptly removed from the reference solution. As shown in FIG. 5A, the surface potential abruptly changes and returns to the original state, exhibiting a change over a comparatively short period of time. In contrast to this, the intramembrane potential changes only slightly and slowly and then reaches slowly an equilibrium. This is because the change in intramembrane potential is caused by ion diffusion into the membrane and diffusion as a physical phenomenon is a gradual phenomenon in terms of time. For these reasons, when a lipid membrane potential is measured after the surface potential is stabilized and before the intramembrane potential does not reach the equilibrium, the influence of the intramembrane potential remains. However, when measurement is repeatedly performed under the same measurement conditions, a change in intra-membrane potential over time can be recognized as constant. As a result, a measured value free from an influence of an intramembrane potential can be obtained in a relative manner (if a difference between two measured values is calculated).

Figure 5B:
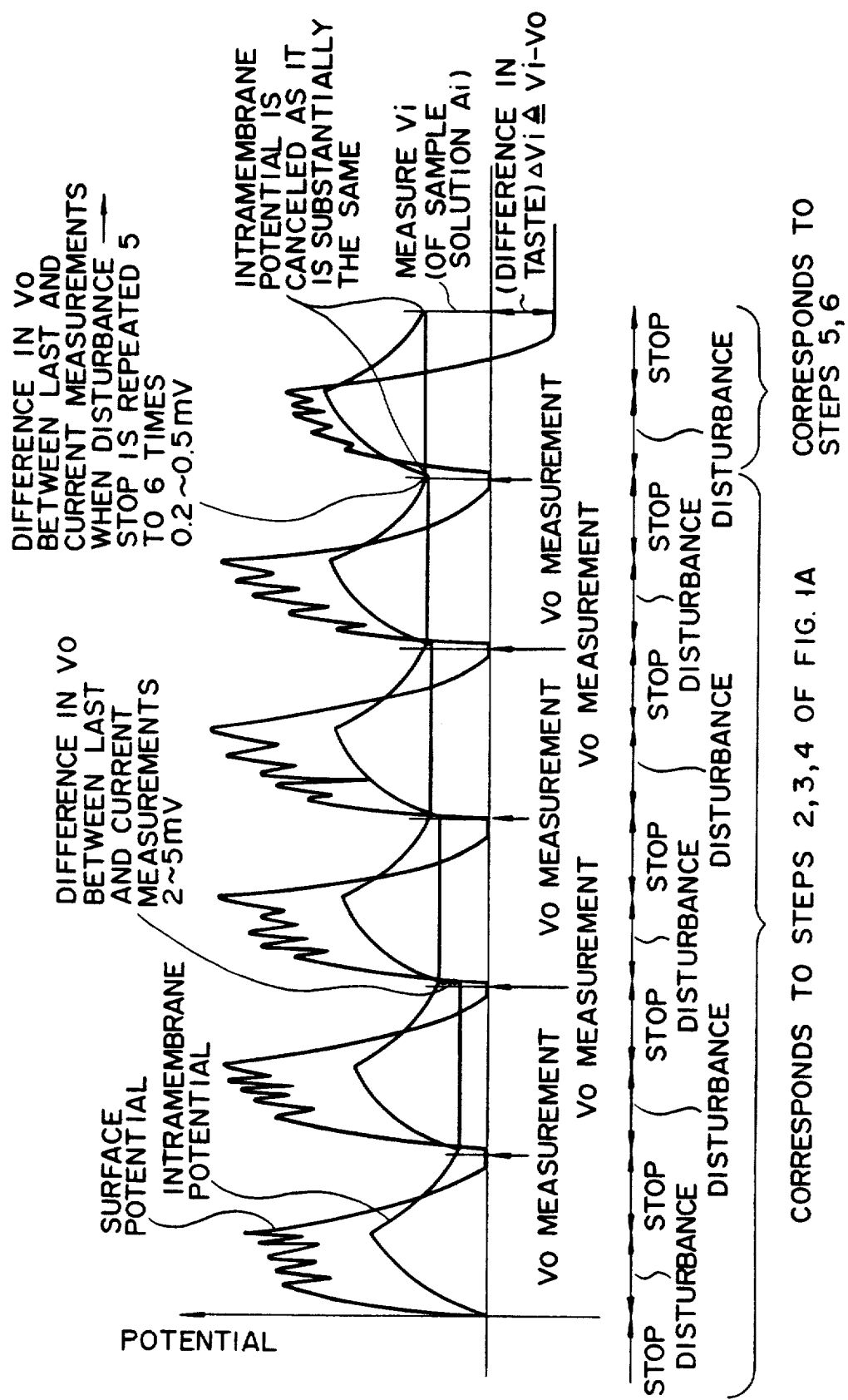

FIG. 5B shows the timings of the actual cyclical measurement including portions corresponding to steps 2, 3, and 4 and steps 5 and 6 in FIG. 1A.

The surface potential is stabilized within a relatively short period of time after the disturbance is stopped, whereas the intramembrane potential gradually reaches the equilibrium. However, when the cycle of disturbance and stop is performed several times (depending on the sample solution to be measured and so on), a difference in potential V0 between the current and last measurements becomes small (e.g., 2 to 5 mV→0.2 to 0.5 mV). If the measurement of a sample solution Ai is performed in accordance with the same cycle (disturbance→stop) when the difference in potential V0 becomes a limit value or less, the difference in potential V0 can be canceled. This is because the intramembrane potentials of the reference solution and the sample solution are substantially the same at each point of measurement even if the intramembrane potential does not reach the equilibrium.

The above will be described in detail as following.

a) The reference solution and the sample has similar tastes each other.

b) The surface potential is stabilized within a relatively short period of time.

c) The intramembrane potential is stabilized in a relatively long period of time.

d) The intramembrane potential is reached a stabilized state different from the above c), by stimulating the membrane, e) After stabilized the surface potential, a variation of Vo or Vi is a variation of the intramembrane potential itself. For example, differences of Vo in measurements shown in FIG. 5B depended on the intramembrane potential, so that the other stabilized state is obtained as described in the above d), f) Values of Vm of the other stabilized state in the above d) represent a substantially equal value in measurements of the reference solution and the sample so that Vm can be canceled.

(3) Measurement is performed during constant repetitive sensor operation. This is employed in order to minimize the influence of intramembrane potential. In order to perform measurement in this manner, firstly, the reference solution must have a composition similar to that of the sample solution to be measured (sometimes one or a mixture of a plurality of sample solutions to be measured is prepared as the reference solution) so that the difference between the sample solution and the reference solution is not very large. Secondly, the taste sensor must be sufficiently dipped in the reference solution. Thirdly, the cycle of removing the taste sensor from the reference solution (canceling dipping in the reference solution), dipping the taste sensor again in the sample solution to be measured, and measuring the membrane potential, must be repeated. It must be confirmed that the fluctuation falls within a predetermined range, and a measured taste value is obtained.

Figure 1C:
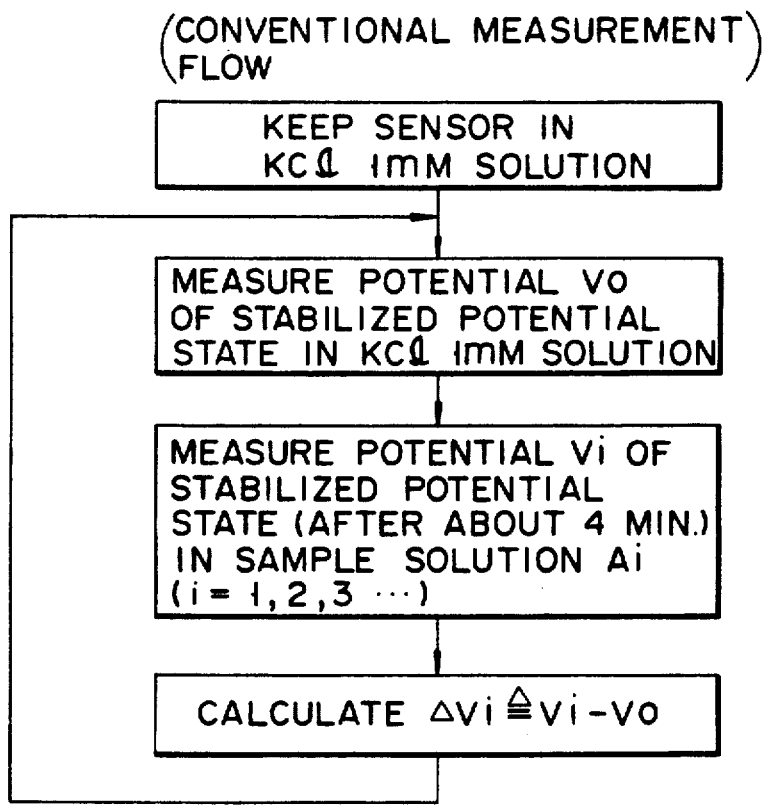

FIG. 1A is a flow chart of the measuring steps employing all of the three means described above. FIG. 1C is a flow chart of the conventional measuring method of a taste using a taste sensor, in which the taste sensor is kept in a potassium chloride solution having a concentration of 1 m mol/l and the potassium chloride solution having a concentration of 1 m mol/l is used as the reference solution. FIG. 1B shows a measuring step I used in steps 2, 4, and 5 of the flow chart of FIG. 1A. Of the flow chart of FIG. 1A, steps 1 to 4 use the method (1) described above, and steps 2, 4, and 5 use the methods (2) and (3) described above.

According to the flow chart of FIG. 1A, (1) since a difference between the reference solution and the sample solution to be measured becomes small, a fluctuation in measurement is decreased. (2) Since the measurement is performed after the surface potential is stabilized and during gradual change of the intramembrane potential, the measurement time is shortened. Furthermore, (3) a change in intramembrane potential can be canceled by a constant repetitive measurement. (4) When the taste sensor is dipped in the reference solution for a sufficient period of time, the operation of the taste sensor can be stabilized. (5) A kind of stimulation is applied to the surface of the taste sensor upon measurement by intermittently dipping the sensor in a solution of the same type as the solution to be measured, resulting in taste measurement with good reproducibility.

Preferred embodiments of the present invention based on the principle described above will be described.

FIG. 1D shows a taste sensing system applied to the following embodiments. Referring to FIG. 1D, reference numerals 101, 102, ..., 10n denote tanks filled with a plurality of samples A1, A2, ..., An to be measured that have tastes similar to each other. Reference numeral 100 denotes a tank filled with a reference solution A0 having a taste similar to the plurality of samples to be measured. The tanks 100, 101, 102, ..., 10n are connected to a pump 214 through pipes 111, 112, ..., 11n, respectively. The pump 214 is controlled by a controller 215 to selectively introduce the reference solution A0 or one of the plurality of samples A1, A2, ..., An to be measured to a sensor 216 through a pipe 210. The sensor 216, a measurement unit 217 that receives a signal from the sensor 216, and a display 218 for displaying measurement data sent from the measurement unit 217 function in the same manner as the respective constituent elements of the multi-channel taste measuring system as shown in FIG. 11.

Note that the controller 215 also controls the sensor 216 and the measurement unit 217 in addition the pump 214 described above and has a function to control the entire taste sensing system in accordance with the flow charts shown in FIGS. 1A and 1B and the taste sensing steps of the respective embodiments to be described later.

EXAMPLE 1

Figure 10A:
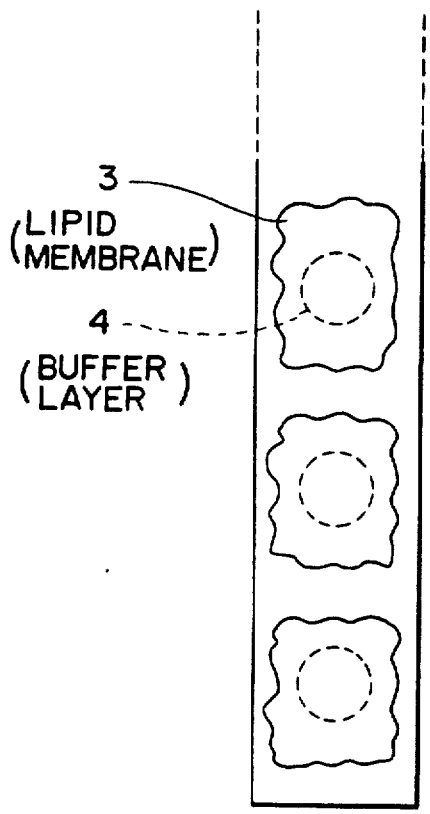
Figure 10B:
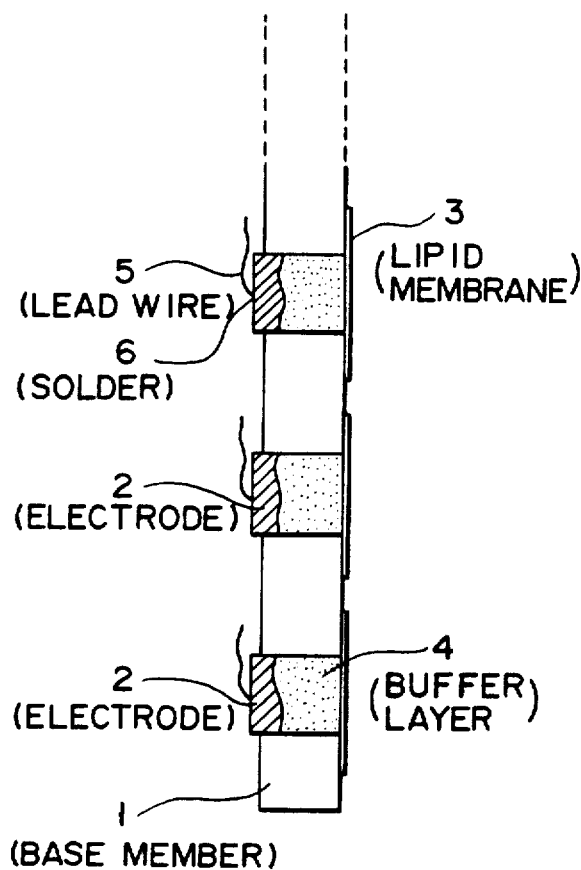
Figure 11:
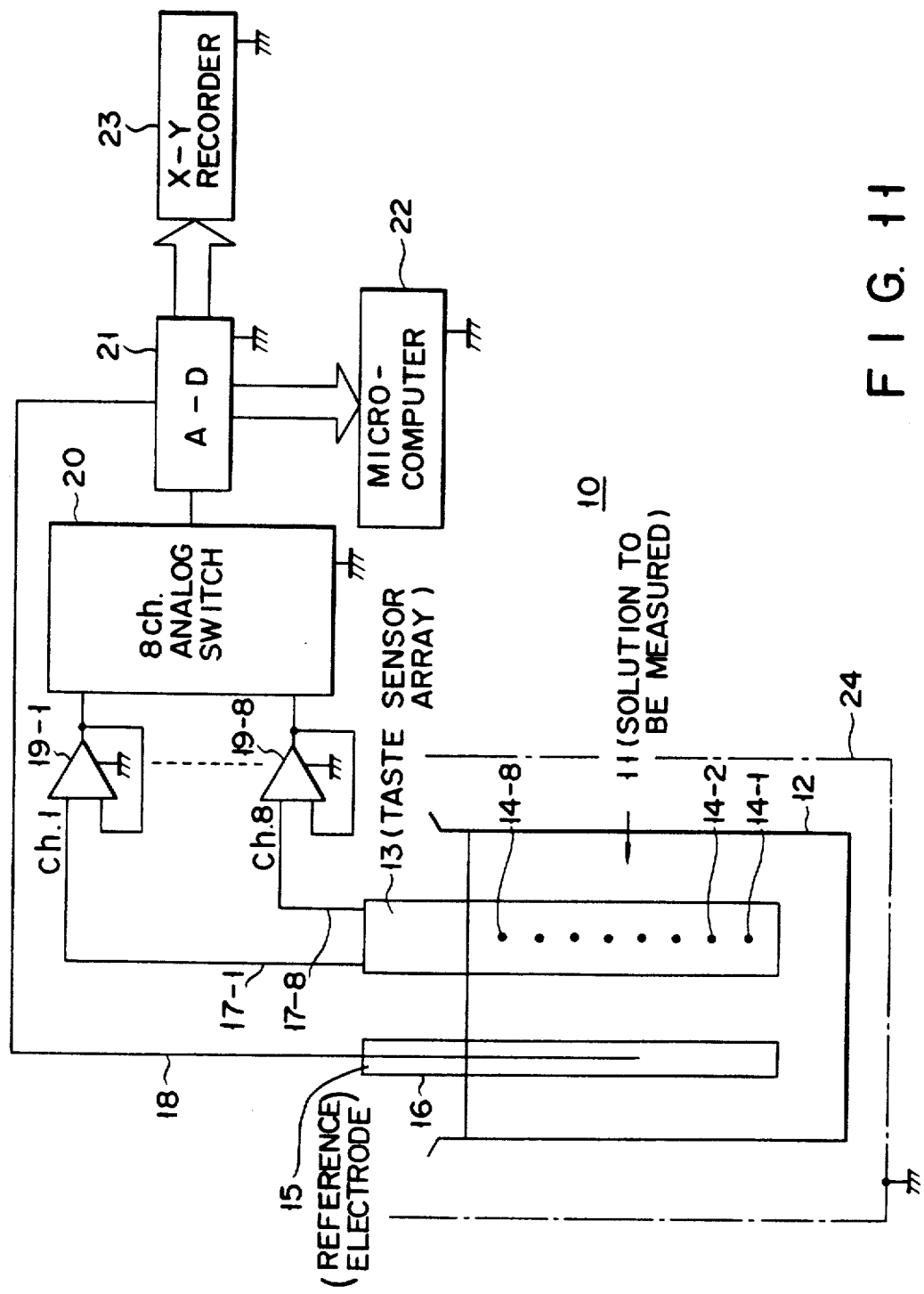
FIG. 11 shows a taste measuring system.
Figure 12:
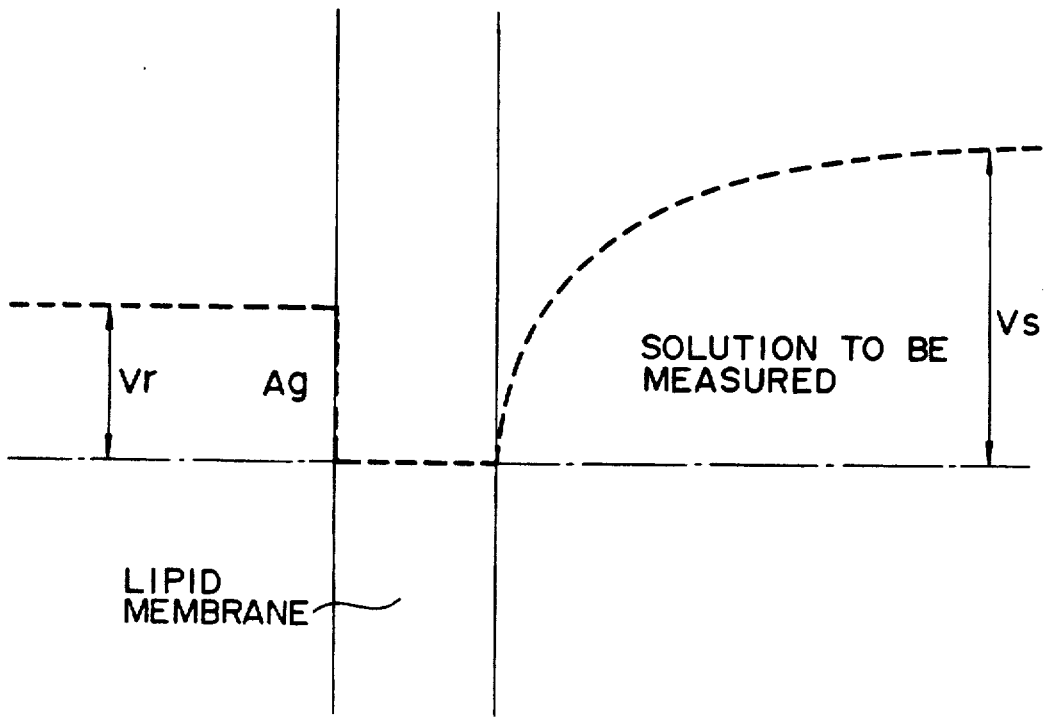
FIG. 12 shows the potential profile of the taste sensor electrodes.

In Example 1, the tastes (to discriminate a difference) of four beverages (A, Al, TL, and P) commercially available in Japan as sports drinks, were measured as samples to be measured by a measuring system shown in FIG. 11 using a taste sensor (refer to FIGS. 10A and 10B) using a lipid membrane as described above. As the lipid membranes used in the taste sensor, 8 types (sequentially denoted as lipid membranes 1 to 8 and the potential signals obtained by them are denoted as 1 to 8 channels) of lipid molecules listed in Table 1 were selected. A solution as a mixture of the four sports drinks A, Al, Tl, and P was prepared as a reference solution A0. The taste sensing steps are as follows:

[0] Dip the taste sensor using the lipid membrane in the reference solution A0 for about 10 hours.

[1] Perform the cycle of dipping and removing the taste sensor in and from the reference solution (for washing) ten times. This treatment may be rephrased to wash the taste sensor with the reference solution (for washing), to intermittently dip the taste sensor in the reference solution, or to stimulate the surface of the lipid membrane of the taste sensor.

[2] Dip the taste sensor in the reference solution prepared for measurement. When 20 seconds elapse, measure the potential of the taste sensor, and determine the measured value as V0.

[3] Repeat the steps [1] and [2] twice or more. After each measurement, discriminate whether or not a difference between the current measured value V0 and the last measured value V0 is a predetermined value or less. If it is the predetermined value or less (i.e., when V0 is stabilized), advance to next step [4].

[4] Remove the taste sensor from the reference solution A0 (for measurement) and wash it with a sample solution to be measured (for washing). Repeat this washing step [4] ten times in the same manner as the step [1].

[5] Dip the taste sensor in a sample solution Ai (for measurement) to be measured. When 20 seconds elapse, measure a potential Vi of the taste sensor. A value $\Delta V = Vi - V0$ is obtained as the taste.

[6] Return to the measuring step [1] and repeat the steps [1], [2], [4], and [5]. When this cycle is repeated a predetermined number of times, end the steps.

Figure 6:
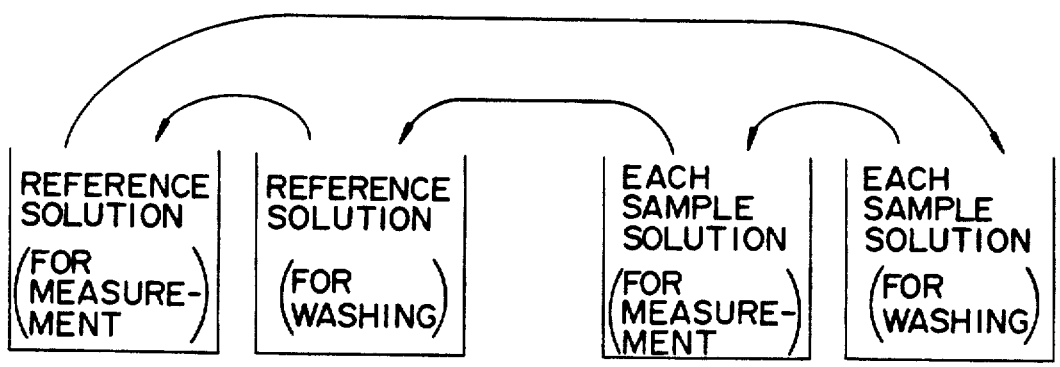
FIG. 6 shows the measuring steps according to the present invention.

FIG. 6 shows these steps.

When there are a plurality of sample solutions to be measured, the order to measure the samples may be determined measurement may be performed repeatedly, and an average may be obtained.

FIGS. 7A (standardized average) and 7B (standardized value) show the measurement results (fj measurements) of 1 to 8 channels. The axis of ordinate represents a potential divided by a standard deviation $\sigma$ of measurement. From the measurement results, it is apparent that in channels 1, 5, and 6, the product types can be discriminated since the variation is considerably small despite that $\Delta V$ is small, that in all of channels 1 to 8, the products can be discriminated from each other, and that products AL and L have similar tastes. The fact that the products AL and L have similar tastes coincides with the determination made by the human sense of taste. It is also apparent that the channels 5 and 6 have a rather high product discriminating ability even when they are used independently. A further reliable discrimination can be performed by totaling the signals of channels 1 to 8.

EXAMPLE 2

A taste sensor using the same lipid membrane as Example 1 is used. The tastes of seven different types of beer commercially available in Japan from manufacturers A, K, S, and Y (of which three types are DA, DK, and DS that are called dry beer; three types are MK, MS, and MY that are called malts beer; and lager beer LK is used as a reference solution) were measured and compared. LK is a beer whose feature is said to be its bitterness. In fact, however, it is difficult to determine taste differences of these types beer by the ordinary people, and impossible to accurately discriminate tastes of the seven types beer, respectively.

Figure 8A:
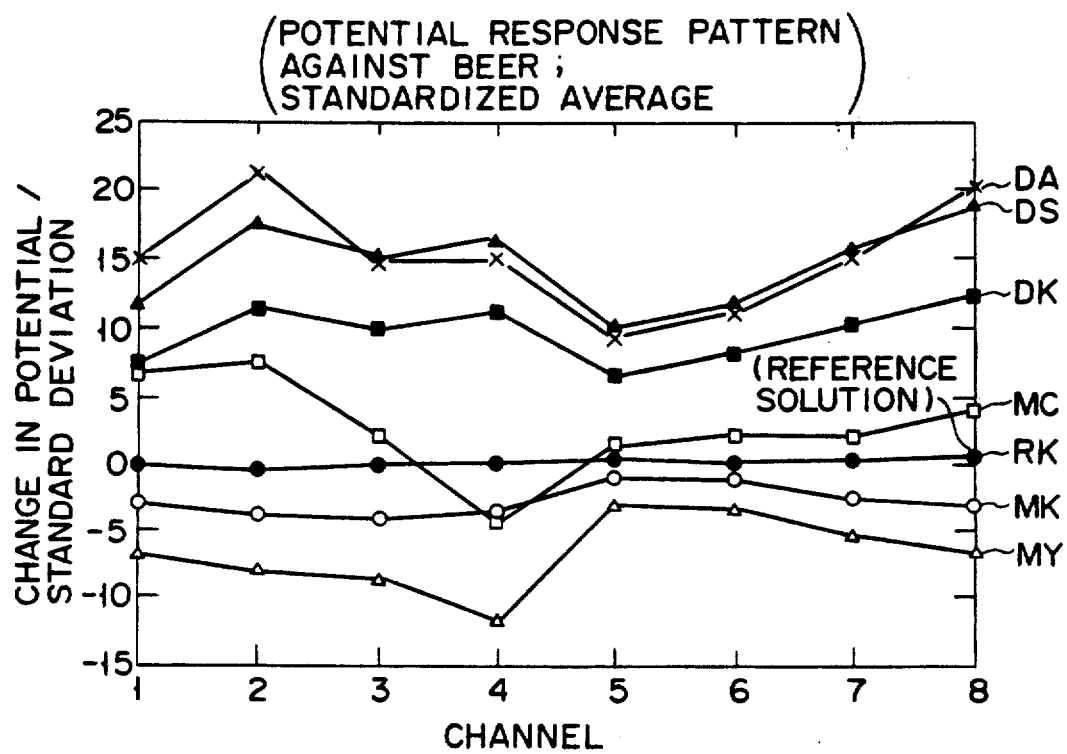
Figure 8B:
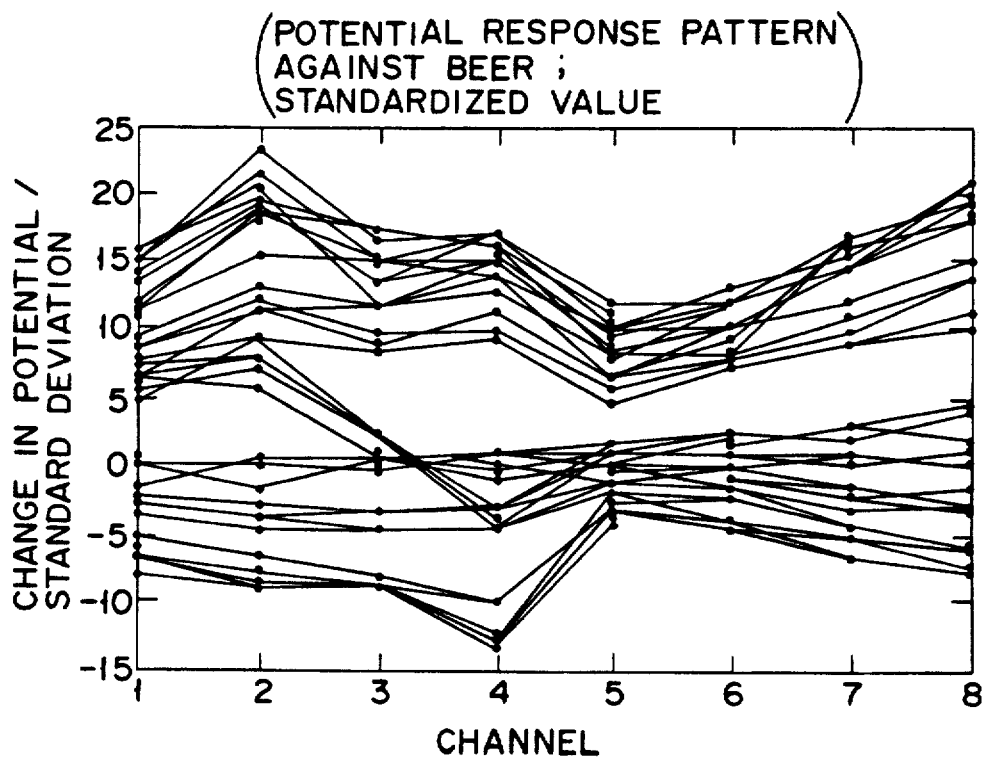
Figure 9:
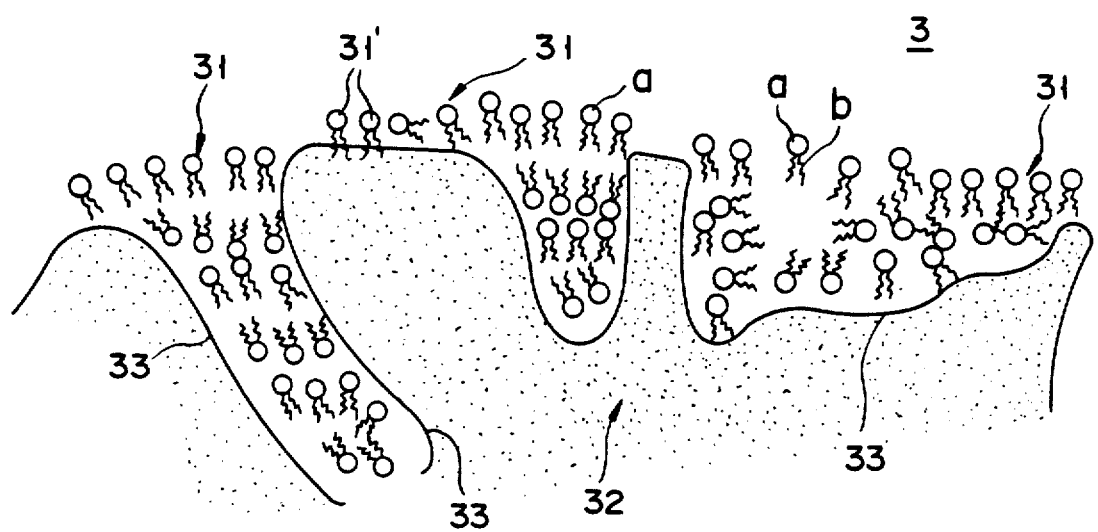
FIG. 9 is a schematic view showing a structure of a lipid membrane for a lipid membrane by an expression method used in a designating method of a chemical substance.

The measuring steps are identical to those described in Example 1. FIG. 8A (standardized average) and FIG. 8B (standardized value) show the measurement results. Channels 1, 2, and 8 have an ability to discriminate the different types of beer. Beers DA and DS have similar tastes, which coincides with the determination made by the human sense of taste.

According to the present invention, in order to sense and measure a taste by a taste sensor using lipid molecules with good reproducibility, a solution similar in composition to a sample solution to be measured is used as a reference solution, the taste sensor is sufficiently dipped in the reference solution, similar stimulations are applied to the taste sensor every measurement cycle, and the measuring time point is selected to be one after the surface potential is stabilized and during gradual change of the intramembrane potential. As a result, the reproducibility of a measured value obtained by the taste sensor is increased, and a variation in the measured value is decreased, enabling taste detection equal to that by the human sense of taste which can conventionally be replaced by nothing.

When the lipid membrane potential of the taste sensor is repeatedly measured and its average is obtained, the taste discriminating ability is further improved.

Regarding beer, a discriminating ability similar to that done by the human sense can be obtained to discriminate beer. For example, the similarity between the dry beers of manufacturers A and C, and the non-similarity between the dry beer of the manufacturer K and those of manufacturers A and C were verified.

In fine, according to the present invention, foods having only a subtle difference in taste can be discriminated with a sufficient reproducibility, thus contributing to quality control of such foods.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. A method for individually measuring a plurality of similar taste sample solutions each including a plurality of taste substances to be tested by using a lipid membrane that is applied to a system of taste reception, said lipid membrane representing response of membrane potential and individually interacting with the plurality of similar taste sample solutions, said method comprising the steps of:
   (a) preparing a reference solution having a taste identical or similar to one of the plurality of similar taste sample solutions;
   (b) measuring the reference solution by using the lipid membrane to obtain a measured value V0 relating to the response of membrane potential;
   (c) measuring one of the plurality of similar taste sample solutions by using the lipid membrane to obtain a measured value Vi relating to the response of membrane potential; and
   (d) calculating a relative value Vi−V0 in accordance with the measured value V0 of the reference solution and the measured value Vi of one of the plurality of similar taste sample solutions,
   wherein steps (b) to (d) are repeatedly executed for each of the plurality of taste sample solutions, and the reproducibility of the relative value Vi−V0 obtained by the lipid membrane is increased, and a variation in the relative value Vi−V0 is decreased.

2. A method according to claim 1, wherein the lipid membrane is dipped in the reference solution for a predetermined period of time prior to the steps (b) to (d).

3. A method according to claim 1, wherein, prior to the steps (b) to (d), a first time starting with dipping the lipid membrane in the reference solution until stabilization of a surface potential of the lipid membrane and a second time until stabilization of an intramembrane potential of the lipid membrane are measured, and both steps measuring the reference solution and the one of the plurality of similar taste sample solutions are performed during the same time period longer than the first time and shorter than the second time.

4. A method according to claim 1, wherein, prior to the steps (b) to (d), measurement is repeatedly performed while intermittently dipping the lipid membrane in the reference solution, and after a change in a measured value falls within a predetermined range, the steps (b) to (d) are performed.

5. A method according to claim 1, wherein the reference solution includes a solution mixture of the plurality of similar taste sample solutions.

6. A method for individually measuring a plurality of similar taste sample solutions each including a plurality of taste substances to be tested by using a lipid membrane that is applied to a system of taste reception, said lipid membrane representing response of membrane potential and individually interacting with the plurality of similar taste sample solutions, said method comprising the steps of:
   (a) preparing a reference solution having a taste identical or similar to one of the plurality of similar taste sample solutions;
   (b) measuring one of the plurality of similar taste sample solutions by using the lipid membrane to obtain a measured value Vi relating to the response of membrane potential;
   (c) measuring the reference solution by using the lipid membrane to obtain a measured value V0 relating to the response of membrane potential; and
   (d) calculating a relative value Vi−V0 in accordance with the measured value V0 of the reference solution and the measured value Vi of one of the plurality of similar taste sample solutions,
   wherein steps (b) to (d) are repeatedly executed for each of the plurality of similar taste sample solutions, and the reproducibility of the relative value Vi−V0 obtained by the lipid membrane is increased, and a variation in the relative value Vi−Vo is decreased.

7. A method for measuring a plurality of similar taste sample solutions each including a plurality of taste substances to be tested by using a lipid membrane that is applied to a system of taste reception, said lipid membrane representing response of membrane potential and individually interacting with the plurality of similar taste sample solutions, said method comprising the steps of:
   biasing the lipid membrane by dipping the lipid membrane in a reference solution having a taste identical or similar to the plurality of similar taste sample solutions;
   periodically stimulating the lipid membrane by intermittently dipping and removing the lipid membrane in and from the reference solution or one of the plurality of similar taste sample solutions a predetermined number of times;

synchronously measuring the response of membrane potential with respect to the reference solution and one of the plurality of similar taste sample solutions at the same timing as that at which the response of membrane potential shows a stabilizing tendency during the stimulating step; and evaluating a relative value between the response of membrane potential with respect to the reference solution and the response of the membrane potential with respect to the one of the plurality of similar taste sample solutions, wherein the reproducibility of the relative value obtained by the lipid membrane is increased, and a variation in the relative value is decreased.

8. A method according to claim 7, wherein a plurality of lipid membranes representing different potential responses are used.

9. A method according to claim 8, wherein evaluation of the relative value is executed based on multi-channel data according to the response of membrane potential of the plurality of lipid membranes.

10. A method according to claim 7, wherein the reference solution has a taste similar to those of the plurality of similar taste sample solutions.

11. A method according to claim 7, wherein the reference solution contains a solution mixture of the plurality of similar taste sample solutions.

12. A method according to claim 7, wherein measurement by the lipid membrane is executed in an order of the reference solution and then one of the plurality of similar taste sample solutions.

13. A method according to claim 7, wherein measurement by the lipid membrane is executed in an order of one of the plurality of similar taste solutions and then the reference solution.

* * * * *